United States Patent [19]

Zeman

[11] Patent Number: 4,613,570

[45] Date of Patent: Sep. 23, 1986

[54] NOVEL THERMOSTABLE, ACIDURIC ALPHA-AMYLASE AND METHOD FOR ITS PRODUCTION

[75] Inventor: Nancy W. Zeman, Sleepy Hollow, Ill.

[73] Assignee: CPC International Inc., Englewood Cliffs, N.J.

[21] Appl. No.: 699,772

[22] Filed: Feb. 8, 1985

[51] Int. Cl.[4] .................. C12P 19/14; C12N 9/28; C12R 1/145

[52] U.S. Cl. .................................. 435/99; 435/202; 435/842

[58] Field of Search .................. 435/202, 203, 99, 842

[56] References Cited

U.S. PATENT DOCUMENTS 4,284,722  8/1981  Tamuri et al. .................... 435/94
4,578,352  3/1986  Katkocin et al. ................. 435/99

FOREIGN PATENT DOCUMENTS 0131253  1/1985  European Pat. Off. .

OTHER PUBLICATIONS

Chiang, et al, *Die Stärke*, 31, 86–92 (1979).
Hobson, et al, *Biochem. J.*, 52, 671–679 (1952).
Hockenhull, et al, *Biochem. J.*, 39, 102–106 (1945).
Ensley, et al, *J. Gen. Appl. Microbiol.*, 21, 51–59 (1975).

*Primary Examiner*—Lionel M. Shapiro
*Attorney, Agent, or Firm*—Stanley M. Parmerter

[57] ABSTRACT

This invention relates to an alpha-amylase enzyme exhibiting thermostability at an acidic pH, produced by a strain of *Clostridium thermohydrosulfuricum*. This enzyme is especially useful for the preparation of glucose-containing syrups from starch.

6 Claims, No Drawings

NOVEL THERMOSTABLE, ACIDURIC ALPHA-AMYLASE AND METHOD FOR ITS PRODUCTION

FIELD OF THE INVENTION

This invention relates to a novel alpha-amylase useful for the hydrolysis of a starch at low pH and to a method for its production by a species of *Clostridium thermohydrosulfuricum* in an anaerobic fermentation.

BACKGROUND OF THE INVENTION

Large quantities of glucose-containing syrups are manufactured by the enzymatic hydrolysis of corn starch. This is generally carried out in two stages. In the first step, the starch is liquefied by treatment with an alpha-amylase enzyme at a pH between 6 and 7. The liquefied starch is then saccharified by means of a glucoamylase enzyme operating at a pH between 4 and 4.5.

The principal alpha-amylases presently used for the first step in the hydrolysis of starch are bacterial alpha-amylases produced by *Bacillus subtilis, Bacillus licheniformis,* and *Bacillus stearothermophilus.* Although these alpha-amylases are comparatively thermostable in solutions above pH 6, they do not exhibit such thermostability at lower pHs.

The alpha-amylases in current use are produced by aerobic microorganisms, i.e., those that require oxygen for growth. There are a few scattered reports of alpha-amylases being produced by anaerobic organisms. Hobson, et al, *Biochem. J.*, 52, 671–679 (1952), reported the isolation of such amylases from two anaerobes, *Clostridium butyricum* and a Streptococcus, present in the rumen of sheep. Both enzymes showed optimum activity at a temperature of 48±1° C. Hockenhull, et al, *Biochem. J.*, 39, 102–106 (1945), found that the anaerobe, *Clostridium acetobutylicum*, also produced an alpha-amylase. This enzyme, which he partially purified, displayed a pH optimum of 4.8 and converted starch completely to maltose. Later Ensley, et al, *J. Gen. Appl. Microbiol.*, 21, 51–59 (1975), studied the production of this enzyme and found that it was induced by the presence of starch in the culture medium. About 40% of the enzyme remained associated with the cells. None of these enzymes showed appreciable stability at higher temperatures.

It would be desirable to hydrolyze starch by conducting the liquefaction and saccharification steps simultaneously in the same reaction mixture. This could be accomplished if alpha-amylases were available that would hydrolyze starch at pH values between 4 and 4.5, where glucoamylase is active. In addition, the alpha-amylase would have to be sufficiently thermostable at this pH to permit the hydrolysis reactions to be carried out at a temperature where the reaction rate is fast enough to be useful.

An alpha-amylase produced by *Clostridium thermoamylolyticum* generally meeting these requirements is disclosed in European Patent Application No. 0 131 253. We have now discovered an alpha-amylase, produced in an anaerobic fermentation reaction by *Clostridium thermohydrosulfuricum*, that shows better starch liquefying properties under these conditions.

SUMMARY OF THE INVENTION

In accordance with the present invention, there is provided a thermostable, aciduric alpha-amylase enzyme derived from *Clostridium thermohydrosulfuricum*. This alpha-amylase enzyme has a molecular weight of about 72,000±3,000 as determined by SDS-polyacrylamide gel electrophoresis, shows a half-life of about 450 minutes when held at 80° C. and pH 4.5 in the presence of 5 mM $Ca^{++}$, has a maximum alpha-amylase activity at a pH of about 5.5 when measured at 80° C., and has a maximum alpha-amylase activity at pH 5.0 at about 60° C.

Also provided, in accordance with this invention, is a process for producing an alpha-amylase enzyme having a molecular weight of about 72,000±3,000 as determined by SDS-polyacrylamide gel electrophoresis, showing a half-life of about 450 minutes when held at 80° C. and pH 4.5 in the presence of 5 mM $Ca^{++}$, having a maximum alpha-amylase activity at a pH of about 5.5 when measured at 80° C., and having a maximum alpha-amylase activity at pH 5.0 at about 60° C. which comprises culturing cells of *Clostridium thermohydrosulfuricum* in a nutrient medium and then isolating the alpha-amylase enzyme from the medium.

Further, in accordance with this invention, is a process for hydrolyzing starch. This process comprises treating an aqueous slurry or solution of starch with the alpha-amylase enzyme of this invention at a pH of 3.5 to 7.0 for a sufficient time to give a solution of starch hydrolyzate.

DETAILED DESCRIPTION OF THE INVENTION

The alpha-amylase of this invention was first obtained from a strain of Clostridium isolated from mud hot springs in Rotaura, New Zealand. The microorganism is a gram variable, obligately anaerobic, motile rod. Sporulation rarely occurs in logarithmically or stationary phase cells, but terminal spores are common in broth cultures stored at room temperature. The optimum temperature for growth is 68° C.–70° C. Little or no growth is observed at 37° C. The optimum pH for growth is about 7.0, although the organism will grow in a pH range of 4.5–8.0. When the organism is grown on starch or maltose, ethanol is the predominant product with smaller amounts of acetic and lactic acids being formed. When the organism is grown on agar plates, it forms opaque, off-white smooth colonies. Cells are rods about 0.6 $\mu$m wide and from 2 $\mu$m to 14.5 $\mu$m in length with an average cell length of about 4–5 $\mu$m. It produces hydrogen sulfide from thiosulfate but not from sulfate and its growth is inhibited by hydrogen. Based on these characteristics, the microorganism is classified as a strain of *Clostridium thermohydrosulfuricum*. This strain has been deposited under the provisions of the Budapest Treaty for deposits of microorganisms for patent purposes. It is available from the American Type Culture Collection, Rockville, Md., as ATCC No. 53016.

The microorganism used for the preparation of the alpha-amylase of this invention is grown under anaerobic conditions in a medium which contains a soluble starch or maltodextrin as the carbohydrate source, a yeast extract plus vitamin and mineral solutions. The presence of maltose in the growth medium increases the amount of alpha-amylase formed, while glucose in the medium inhibits the formation of alpha-amylase. The optimum pH of the fermentation medium for the production of alpha-amylase is about 6.5–7.0. The alpha-amylase is excreted into the fermentation medium.

The alpha-amylase enzyme was purified by removing the cells from the fermentation medium followed by precipitation of extraneous matter with calcium chloride. The enzyme solution was concentrated and further refined by adsorption of the amylase on granular starch. The partially purified amylase was removed from the starch and further purified by chromatography on an Ultrogel column. The purified enzyme had a molecular weight of 72,000±3,000 as determined by sodium dodecyl sulfate (SDS) polyacrylamide gel electrophoresis.

In the following descriptions of the preparation and properties of the alpha-amylase enzyme, all references to parts and percentages are by weight, unless expressly indicated to be otherwise.

alpha-Amylase Assay

The solution to be analyzed is diluted with 0.0025 M calcium chloride solution to give a final concentration of about 0.25 unit of activity per ml. One ml of properly diluted enzyme solution is added to 10 ml of a 1% soluble starch solution containing 0.03 M acetic acid buffer (pH 6.0) and 0.03 M calcium chloride. The reaction is carried out for 10 minutes at 60° C. One ml of the reaction solution is put in a 100-ml graduated flask containing 50 ml of 0.02 N hydrochloric acid, and after adding 3 ml of 0.05% iodine solution thereto, the total volume is made up to 100 ml by the addition of water. The blue color which develops is measured for absorbance at 620 nm. The amount of the enzyme required to decompose 10 mg/starch in 1 minute is defined as 1 unit.

$$1 \text{ unit} = \frac{D_o - D_s}{D_o} \times \frac{50}{10 \times 10} \times (\text{dilution factor})$$

where $D_o$ = absorbance of control solution (water is added instead of the enzyme solution)

$D_s$ = absorbance of the reaction solution

Preparation of alpha-Amylase

Extracellular alpha-amylase enzyme preparation was obtained from *Clostridium thermohydrosulfuricum*, ATCC No. 53016.

Medium preparation and cultivation of samples were carried out using standard anaerobic techniques as described by Hungate, R. E., "A Roll Tube Method for Cultivation of Strict Anaerobes", in *Methods in Microbiology*, edited by J. R. Norris and D. W. Ribbons, Vol. 3B, Academic Press, New York, 1969, pp. 117–132, and by Miller and Wolin, *Appl. Microbiol.*, 27, 985 (1974).

The medium used to produce seed and to maintain the stock culture of the organism had the following composition:

| Seed Medium | |
|---|---|
| Ingredients | Concentration (g/l) |
| Starch (Lintner) | 20 |
| KH$_2$PO$_4$ | 1.5 |
| NH$_4$Cl | 0.5 |
| Na$_2$HPO$_4$.12H$_2$O | 4.2 |
| MgCl$_2$ | 0.18 |
| Yeast Extract | 2.0 |
| Vitamin Solution | 0.5 ml/l |
| Mineral Solution | 50 ml/l |
| Resazurin (0.1%) | 1 ml/l |
| Reducing Solution | 40 ml/l |

| Vitamin Solution | |
|---|---|
| Vitamins | mg/l |
| Biotin | 2 |
| Folic Acid | 2 |
| Pyridoxine.HCl | 10 |
| Riboflavin | 5 |
| Thiamine.HCl | 5 |
| Nicotinic Acid | 5 |
| Pantothenic Acid | 5 |
| B$_{12}$ | 0.1 |
| p-Aminobenzoic Acid | 5 |
| Thioctic Acid | 5 |

| Reducing Solution | |
|---|---|
| Ingredients | Amount |
| NaOH (0.2 N) | 200 ml |
| Na$_2$S.9H$_2$O | 2.5 g |
| Cysteine HCl.H$_2$O | 2.5 g |

| Mineral Solution | |
|---|---|
| Ingredients | mg/100 ml |
| Nitrilotriacetic Acid | 1500 |
| MgSO$_4$.7H$_2$O | 3000 |
| MnSO$_4$.H$_2$O | 500 |
| NaCl | 1000 |
| FeSO$_4$.7H$_2$O | 100 |
| Co(NO$_3$)$_2$.6H$_2$O | 100 |
| CaCl$_2$ | 100 |
| ZnSO$_4$.7H$_2$O | 100 |
| KAl(SO$_4$)$_2$ | 10 |
| H$_3$BO$_3$ | 10 |
| Na$_2$MoO$_4$.2H$_2$O | 10 |
| Na$_2$SeO$_3$ | 1 |

Viable cells could be maintained in the seed medium at room temperature for at least 6 months. The strain was preserved by mixing 1 ml of a logarithmically growing culture with 5 ml of 50% anaerobic glycerol solution and then freezing at −70° C. In order to grow the microorganisms for production of enzyme, sterile seed medium was inoculated with cells and incubated at 60°–68° C. under anaerobic conditions for approximately 24 hours. This produced rapidly-growing cells which were used to inoculate a fermentor. The volume of inoculum was from 1 to 5% of the volume of the growth medium in the fermentor. This medium had the following composition:

| Growth Medium | |
|---|---|
| | g/100 ml |
| Maltrin 100[a] | 1 |
| PROFLO[b] | 5 |
| Prymex[c] | 1 |
| MgSO$_4$.7H$_2$O | 0.5 |
| CaCl$_2$.2H$_2$O | 0.06 |
| MnCl$_2$.2H$_2$O | 0.001 |
| KH$_2$PO$_4$ | 0.13 |
| (NH$_4$)$_2$HPO$_4$ | 1 |

[a] A 10 dextrose equivalent starch hydrolyzate available from the Grain Processing Company, Muscatine, Iowa.
[b] A cottonseed meal available from Traders Oil Mill Company, Fort Worth, Texas.
[c] A yeast extract available from Amber Laboratories, Milwaukee, Wisconsin.

The pH of the medium was adjusted to 6.5. Production runs were made in a 14-liter fermentor using 10 liters of medium. The yield of extracellular alpha-amylase was 0.1 to 1.5 units per ml of fermentation broth.

Purification of the Enzyme

The crude alpha-amylase enzyme was purified by the following procedure. The fermentation broth was first filtered through glass wool to remove a gummy insoluble substance. Cells were then removed from the filtrate by means of a Sharples continuous scroll centrifuge, Model 741-24/8R4 (Sharples Corp., Philadelphia, Pa.), operated at 45 psi pressure. To the clear supernatant was added sufficient calcium chloride to give a final concentration of about 1.5–3.0% w/v and the mixture was stirred for 10 minutes. The bulky precipitate was removed by filtration and discarded. The clear, amber-colored filtrate was then concentrated by an Amicon hollow-fiber (HP-10) concentrator, type AC2, available from the Amicon Corp., Danvers, Mass. Concentration was carried out until the volume was between 500 and 1000 ml before concentrated ammonium hydroxide was added to bring the pH to 6. The addition of ammonium hydroxide caused a second precipitate to form, which was removed by filtration. The concentrated filtrate was further purified by treatment with granular starch which had been equilibrated with a sodium acetate buffer solution containing 50 mM sodium acetate at pH 6 and 5 mM $Ca^{++}$. One gram of starch was used for every 300 units of enzyme. The mixture of starch and enzyme solution was stirred gently at room temperature for 60 minutes before the solid was collected by vacuum filtration. The starch cake containing bound alpha-amylase was resuspended in a small volume of ice cold sodium acetate buffer solution and again filtered after brief stirring. This washing procedure was repeated three times with cold sodium acetate buffer. Washed starch cake was suspended in fresh sodium acetate buffer and incubated at 60° C. with occasional stirring for 60 minutes. During this time, the adsorbed alpha-amylase hydrolyzes the starch sufficiently to be released into solution. The mixture was then filtered, and the colorless filtrate, containing the alpha-amylase enzyme, was concentrated to a volume of about 3 ml by means of an Amicon ultrafiltration cell (Amicon Corp., Danvers, Mass.) fitted with YM10 membrane of a 10,000 $M_r$ cut. The mixture was clarified by centrifugation at 10,000× g for 10 minutes before the supernatant was loaded on a 1.5×85 cm column of acrylamide agarose gel, Ultrogel AcA 54 (LKB Producter AB, Bromma, Sweden) which had been previously equilibrated with 50 mM sodium acetate buffer containing 100 mM NaCl and 5 mM $Ca^{++}$. The column was eluted with the same buffer at a flow rate of 16 ml/hr. Three ml fractions were collected and checked for alpha-amylase activity. The fractions containing enzyme activity were combined and stored in a refrigerator. Their protein content was determined by the method of Lowry, et al, J. Biol. Chem., 193, 265–275 (1951) using bovine serum albumin as a standard. The results of the purification procedure are given in Table I. They show that the purified alpha-amylase has a specific activity of about 22 enzyme units per mg of protein.

TABLE I

PURIFICATION OF ALPHA-AMYLASE FROM ATCC NO. 53016

| Procedure | Volume (ml) | Units Per ml | Units Per mg Protein | Yield (%) |
| --- | --- | --- | --- | --- |
| Fermentation Broth | 350 | 0.36 | 0.011 | 100 |
| $CaCl_2$ Treatment and Ultrafiltration | 315 | 0.34 | 0.015 | 86.0 |
| Starch Affinity | 37 | 1.0 | 1.74 | 29.4 |
| Ultrogel AcA 54 Column | 42 | 0.59 | 21.9 | 19.7 |

Molecular Weight of the Enzyme

The purified alpha-amylase was determined to be homogeneous by its migration as a single protein band when subject to polyacrylamide gel electrophoresis. The molecular weight of the enzyme was determined by SDS-polyacrylamide gel electrophoresis according to the procedure of Laemmli, U. K., Nature, 227, 680–685 (1970). By comparing the mobility of the alpha-amylase with that of standard proteins, a molecular weight of 72,000±3,000 was estimated for the enzyme. This is considerably larger than the molecular weight of 51,000 determined for a purified sample of Thermamyl 60L, an alpha-amylase derived from B. licheniformis. Taka-Therm, an alpha-amylase derived from another strain of B. licheniformis, has a reported molecular weight of 62,000 (Chiang, et al, Die Stärke, 31, 86–92 (1979)).

The molecular weight of the present alpha-amylase is near that of the alpha-amylase produced by Clostridium thermoamylolyticum (75,000±3,000, European Patent Application No. 0 131 253). However, the present alpha-amylase has a much longer half-life at pH 4.5. This makes it more suitable as a starch-hydrolyzing enzyme in the pH range where glucoamylase is most active.

Thermostability of the Enzyme

The thermostability of the purified alpha-amylase was compared with that of three other known thermostable alpha-amylases. The enzymes were diluted with 50 mM acetate buffer of the desired pH, containing 5 mM $Ca^{++}$, to make solutions containing 1 unit of enzyme activity per milliliter. The solutions were incubated in taped screw-capped vials in a water bath at 80° C. and 90° C. At appropriate time intervals (usually 15, 30, 45, 60 and 90 minutes), vials were removed from the water bath and immediately cooled in an ice bath. Residual enzyme activity was assayed at 60° C. using the standard assay procedure. The half-life of the enzyme was calculated by linear regression. Results given in Table II indicate that the enzyme of the present invention has much greater thermostability than the enzymes from B. stearothermophilus, B. licheniformis, and Clostridium thermoamylolyticum. It has a half-life of greater than 7 hours at pH 4.5 and 80° C.

TABLE II

THERMOSTABILITY OF ALPHA-AMYLASE

| | Half-Life (minutes) | |
| --- | --- | --- |
| Enzyme | 90° C., pH 6 | 80° C., pH 4.5 |
| alpha-Amylase of this Invention | 380 | 450 |
| Thermamyl[a] | 266 | 13 |
| alpha-Amylase of B. stearothermophilus[b] | 108 | 22 |
| alpha-Amylase of | 115 | 66 |

TABLE II-continued

THERMOSTABILITY OF ALPHA-AMYLASE

| Enzyme | Half-Life (minutes) | |
|---|---|---|
| | 90° C., pH 6 | 80° C., pH 4.5 |
| C. thermoamylolyticum[c] | | |

[a] An alpha-amylase from *B. licheniformis* available from Novo Laboratories, Wilton, Connecticut.
[b] Tamuri, et al, U.S. Pat. No. 4,284,722.
[c] Katkocin, et al, European Patent Application No. 0 131 253.

pH Effect on the Enzyme

The alpha-amylase enzyme activity was analyzed by the standard procedure except that the pH of the substrate was varied from 3.5 to 7.0 using 100 mM buffer solutions of the following composition: citrate (pH 3.5), acetate (pH 4 to 6), and HEPES (pH 6.5 to 7.0). The relative activities at various pHs given below indicate that the enzyme shows maximum activity at pH 5.0 at 60° C. and at pH 5.5 at 80° C.

| pH | Percent of Maximum Activity | |
|---|---|---|
| | 60° C. | 80° C. |
| 3.5 | 23.6 | 0 |
| 4.0 | 70.9 | 48.4 |
| 4.5 | 99.3 | 93.0 |
| 5.0 | 100 | 98.2 |
| 5.5 | 97.5 | 100 |
| 6.0 | 88.1 | 97.4 |
| 6.5 | 79.0 | 95.0 |
| 7.0 | 72.1 | 82.6 |

Temperature Optimum for the Enzyme

The effect of the reaction temperature on the purified enzyme was determined by performing the standard assay for alpha-amylase activity after incubating an enzyme solution at various temperatures and pH values for 10 minutes. At pH 6, the temperature optimum is $\geq 90°$ C. At pH 4.5, the temperature for maximum activity was at 80°–85° C. with 75% of the maximum activity being observed at 70° C. and over 90% of the maximum activity being observed at 90° C.

The foregoing tests demonstrate that there is provided by this invention a novel alpha-amylase enzyme that hydrolyzes starch at pH values between 4 and 4.5. Furthermore, the amylase is sufficiently thermostable at this pH to permit its use to hydrolyze starch at a temperature where the reaction rate is fast enough to be useful.

While the invention has been described with specific embodiments thereof, it will be understood that it is capable of further modification and adaptations or variations as apparent to those skilled in the enzyme and starch hydrolysis art.

What is claimed is:

1. An alpha-amylase enzyme derived from *Clostridium thermohydrosulfuricum*, said enzyme having a molecular weight of about 72,000±3,000 as determined by SDS-polyacrylamide gel electrophoresis, showing a half-life of about 450 minutes when held at 80° C. and pH 4.5 in the presence of 5 mM $Ca^{++}$, having a maximum alpha-amylase activity at a pH of about 5.5 when measured at 80° C., and having a maximum alpha-amylase activity at pH 5.0 at about 60° C.

2. The alpha-amylase enzyme of claim 1 derived from the strain of *Clostridium thermohydrosulfuricum* ATCC No. 53016, mutants and variants thereof.

3. A process for producing an alpha-amylase enzyme having a molecular weight of about 72,000±3,000 as determined by SDS-polyacrylamide gel electrophoresis, showing a half-life of about 450 minutes when held at 80° C. and pH 4.5 in the presence of 5 mM $Ca^{++}$, having a maximum alpha-amylase activity at a pH of about 5.5 when measured at 80° C., and having a maximum alpha-amylase activity at pH 5.0 at about 60° C. which comprises culturing cells of *Clostridium thermohydrosulfuricum* in a nutrient medium and then isolating the alpha-amylase enzyme from the medium.

4. The process of claim 3 wherein the cells of *Clostridium thermohydrosulfuricum* are those of strain ATCC No. 53016, mutants and variants thereof.

5. A process for hydrolyzing starch comprising treating an aqueous slurry or solution of starch with the alpha-amylase enzyme of claim 1 at a pH of 3.5 to 7.0 for a sufficient time to give a solution of starch hydrolyzate.

6. The process of claim 5 wherein the conversion is conducted at a temperature in the range of from about 50° C. to about 100° C. at a pH of about 4.0 to about 6.0.

* * * * *